United States Patent
Verzini et al.

(10) Patent No.: US 9,604,915 B2
(45) Date of Patent: Mar. 28, 2017

(54) CYCLOPROPANATION OF SUBSTITUTED PHENYLACETONITRILES OR PHENYL ACETATES

(71) Applicant: ZACH SYSTEM S.P.A., Bresso (MI) (IT)

(72) Inventors: Massimo Verzini, Bresso (IT); Livius Cotarca, Bresso (IT); Alberto Guidi, Bresso (IT); Alfonso Melloni, Bresso (IT); Paolo Maragni, Bresso (IT)

(73) Assignee: ZACH SYSTEMS S.P.A., Bresso (IT)

( * ) Notice: Subject to any disclaimer, the term of this patent is extended or adjusted under 35 U.S.C. 154(b) by 0 days.

(21) Appl. No.: 14/894,687

(22) PCT Filed: Jun. 20, 2014

(86) PCT No.: PCT/EP2014/063077
§ 371 (c)(1),
(2) Date: Nov. 30, 2015

(87) PCT Pub. No.: WO2014/206897
PCT Pub. Date: Dec. 31, 2014

(65) Prior Publication Data
US 2016/0102049 A1    Apr. 14, 2016

(30) Foreign Application Priority Data
Jun. 24, 2013  (EP) .................................... 13173370

(51) Int. Cl.
C07C 253/30    (2006.01)
C07C 51/353    (2006.01)
C07C 67/343    (2006.01)

(52) U.S. Cl.
CPC .......... *C07C 253/30* (2013.01); *C07C 51/353* (2013.01); *C07C 67/343* (2013.01); *C07C 2101/02* (2013.01)

(58) Field of Classification Search
CPC ... C07C 253/30; C07C 51/353; C07C 67/343; C07C 2101/02
See application file for complete search history.

(56) References Cited

U.S. PATENT DOCUMENTS

2009/0312558 A1* 12/2009 Bhujbal ................ C07C 253/30
548/267.8
2011/0039934 A1*  2/2011 Pivetti ..................... C07C 51/09
514/570

OTHER PUBLICATIONS

Arava et al. "Efficient cyclopropanation of active methylene compounds. A serendipitous discovery" Tetrahedron Letters 2005, 46, 7247-7248.*
Schiefer et al. "Inhibition of Amyloidogenesis by Nonsteroidal Anti-inflammatory Drugs and Their Hybrid Nitrates" J. Med. Chem. 2011, 54, 2293-2306.*
Gao et al. "Vicinal Diol Cyclic Sulfates: Like Epoxides Only More Reactive" J. Am. Chem. Soc. 1988, 110, 7538-7539.*
Guillaume et al. "Cyclopropanation of dibenzylaminoacetonitrile evaluation of 1,2-dibromides and cyclic 1,2-sulfates as dielectrophiles" Bull. Chem. Soc. Fr. 1994, 131, 391-396.*
Arava V, et al., "Efficient cyclopropanation of active methylene compounds. A serendipitous discovery", Tetrahedron letters, Pergamon, vol. 46, No. 42, Oct. 17, 2005, pp. 7247-7248.
International Search Report and written opinion of PCT/EP2014/063077 of Jan. 29, 2015.

* cited by examiner

*Primary Examiner* — Michael Barker
*Assistant Examiner* — Amanda L Aguirre
(74) *Attorney, Agent, or Firm* — Silvia Salvadori, P.C.; Silvia Salvadori

(57) ABSTRACT

The present invention relates to a process for the cyclopropanation with ethylene carbonate or ethylene sulfate of a compound of formula (II): wherein G is —CN or —COOR in which R is a $C_1$-$C_4$ straight or branched alkyl X and Y are independently selected from the group consisting of hydrogen, fluorine, chlorine, bromine, iodine, $R_1O$— and $R_1S$— wherein $R_1$ is C1-C4 straight or branched alkyl chain.

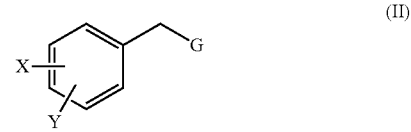

14 Claims, No Drawings

CYCLOPROPANATION OF SUBSTITUTED PHENYLACETONITRILES OR PHENYL ACETATES

This application is a U.S. national stage of PCT/EP2014/063077 filed on 20 Jun. 2014, which claims priority to and the benefit of European Application No. EP13173370.1 filed on 24 Jun. 2013, the contents of which are incorporated herein by reference in their entireties.

The present invention relates to a process for the cyclopropanation of substituted phenylacetonitriles or phenyl acetates to give substituted 1-phenylcyclopropanenitriles and the corresponding carboxylic esters.

Substituted 1-phenylcyclopropanenitriles and the corresponding carboxylic esters are intermediates for the synthesis of drugs useful in the prevention and treatment of neurodegenerative diseases, in particular Alzheimer's disease (WO 2004/074232; WO2009/149797; WO 2011/015287).

In general the cyclopropanation reaction on reactive methylene groups is carried out using of 1,2-dibromo ethane or 1,2-dichloroethane to which toxicological concerns might be associated.

Another compound studied as alkylating reagent in the cyclopropanation reaction on the reactive methylene group of arylacetonitriles is ethylene carbonate (Arava et al. Tetrahedron Letters 46 (2005) 7247-7248).

Ethylene carbonate is known to give cyclopropanation on the reactive methylene group of arylacetonitriles (Arava et al. Tetrahedron Letters 46 (2005) 7247-7248). The yield of the reaction is lower than 55% and the obtained compounds are unstable in the reaction mixture. Therefore the end products have an high content of impurities.

It has now been found that the cyclopropanation reaction with ethylene carbonate can be applied to the compounds of Formula (II) as reported below, under particular conditions to obtain of the corresponding cyclopropane derivatives in high yields.

Furthermore it has been found that high yields can also be obtained using ethylene sulfate as reagent.

The present invention provides a process for the preparation of a compound of formula (I):

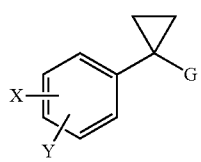
(I)

wherein G is —CN or —COOR in which R is a $C_1$-$C_4$ straight or branched alkyl, X and Y are independently selected from the group consisting of hydrogen, fluorine, chlorine, bromine, iodine, $R_1O$— and $R_1S$— wherein $R_1$ is C1-C4 straight or branched alkyl chain;

said process comprising the step of reacting a compound of formula (II):

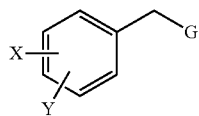
(II)

wherein G, X and Y are as defined above, with a compound of formula (III):

(III)

wherein Z is CO or $SO_2$ in the presence of a base,
with the proviso that:
i) when Z is CO the reaction is carried out at a temperature ranging from 120° C. to 180° C. and the molar ratio between the compound of formula (II) and the compound of formula (III) is from 1:10 and 1:30.
ii) when G is —$COOR_2$ then Z is $SO_2$;
to obtain a compound of formula (I).

X and Y may be in any position of the phenyl ring. Preferably X is in position 4 and Y is in position 3.

Straight chain or branched $C_1$-$C_4$ alkyl may be methyl, ethyl, n-propyl, isopropyl, n-butyl, isobutyl, sec-butyl, tert-butyl, preferably ethyl.

G is preferably —CN or —COOEt.

X is preferably bromine, $CH_3O$— or $CH_3S$—.

Y is preferably hydrogen or fluorine.

The base used in the reaction is preferably selected from the group consisting of sodium, potassium or lithium tert-butylate, potassium carbonate, sodium hydride, lithium bis(trimethylsilyl)amide (LiHMDS), lithium diisopropylamide (LDA).

When Z is CO, i.e. the compound of formula (III) is ethylene carbonate, the reaction may be carried out either without a solvent or in an aprotic organic solvent such as dimethoxyethane (DME), dimethylformamide (DMF), dimethylsulfoxide (DMSO), tetrahydrofuran (THF), toluene, N-methyl-2-pyrrolidone (NMP), toluene.

The reaction is carried out preferably at a temperature ranging 130° C.-180° C. The temperature may depend on the kind of base used in the reaction, for example when the base is sodium carbonate the reaction is carried out preferably at a temperature ranging from 160° C. to 180° C. When the base is lithium tertbutylate the reaction is carried out preferably at a temperature ranging from 120° C. to 140° C., most preferably at 130° C.

The molar ratio between the compound of formula (II) and ethylene carbonate is preferably from 1:20 to 1:30.

The stability of the reaction product of formula (I) in the reaction mixture, and therefore the yield of the reaction, is increased when a catalyst is added to the reaction mixture. The catalyst is a compound able to complex alkaline metal cations which is preferably selected from the group consisting of polyethylene glycols (PEG), phosphonium salts, crown ethers.

Preferably the catalyst is selected from the group consisting of PEG-200, PEG-6000.

Preferably the compound of formula (II) and the catalyst are present in a molar ratio ranging from 1:0.02 to 1:2.

When Z is $SO_2$, i.e. the compound of formula (III) is ethylene sulfate, the reaction may be carried out in an aprotic organic solvent such as dimethoxyethane (DME), dimethylformamide (DMF), dimethylsulfoxide (DMSO), tetrahydrofuran (THF), N-methyl-2-pyrrolidone (NMP), toluene, at a temperature ranging from −20° C. to reflux, preferably from −20° C. to 20° C.

Preferably the molar ratio between the compound of formula (II) and ethylene sulfate is from 1:1 to 1:1.5 and most preferably from 1:1.1 to 1:1.2.

The compounds of formula (II) wherein G is CN are commercial products or they can be prepared by known methods.

The compounds of formula (II) wherein G is $COOR_2$ are commercial compounds or can be prepared from the corresponding compound of formula (I) wherein G is CN according to known methods such as the Pinner reaction (EP0253501A2; JOC 2010, 75, 945-947).

The compounds of formula III are an commercial compounds.

The invention is illustrated in greater detail in the following Examples.

EXAMPLE 1

Cyclopropanation of 4-bromo-3-fluorophenylacetonitrile (II) with ethylene carbonate (III) to give 4-bromo-3-fluorophenyl-cyclopropanenitrile (I)

Ethylene carbonate (370.2 g, 4.204 mol, 30.0 eq.) was loaded in a 500 ml reactor at room temperature and heated to an internal temperature of 40° C. till all the solid melted. Then 1.4 g of PEG-200 (0.007 mol, 0.05 eq.) and 30.0 g of 4-bromo-3-fluorophenylacetonitrile (0.140 mol, 1.0 eq.) were charged in the reactor. Potassium tert-butoxide (31.4 g, 0.280 mol, 2.0 eq.) was added portion-wise, under stirring, to the resulting clear colorless solution. The internal temperature rose up to 60° C. Then, the mixture was heated to 130° C. and kept under stirring for 8 hours. The mixture was cooled to 40° C. and then 105 g of toluene and 240 g of deionised water were added. The mixture was kept under stirring for 15 minutes at 40° C. and then stirring was stopped. After 15 minutes two layers were separated: a lower organic clear red phase and an upper aqueous colorless phase. The organic solution was reloaded into the reactor and heated to an internal temperature of 40° C. 240 g of deionised water were added.

The mixture was kept under stirring for 15 minutes at 40° C. and then stirring was stopped. After 30 minutes the yellowish opalescent aqueous layer (lower) was discarded and the organic phase was washed again two times with 240 g of deionised water. After 30 minutes, the yellowish opalescent aqueous layer was discarded. The organic solution was warmed to 80° C. and the volatile solvents were removed under reduced pressure until 36 ml as the final volume. A solution 9.6 g of isopropyl alcohol was added. The solution was cooled from 80° C. to 50° C. in 30 minutes and a small amount of seed was added. The crystallization mixture was cooled from 50° C. to 0° C. in 60 minutes. The suspension was stirred for at least 60 minutes then filtered washing three times with 9.0 g of a toluene/isopropyl alcohol mixture (1/1.25 w/w). The wet product was dried under vacuum at 40° C. for 15-18 hours. 22.7 g of a pale yellow solid were obtained (purity=99.94%; molar yield=68%).

EXAMPLE 2

Cyclopropanation of 4-bromo-3-fluorophenylacetonitrile (II) with ethylene sulfate (III) to give 4-bromo-3-fluorophenyl-cyclopropanenitrile (I)

24 ml of lithium bis(trimethylsilyl)amide (1M in THF, 24 mmol, 2.2 eq.) were loaded at T=−20° C. in a 50 ml dried reactor under nitrogen. 2.34 g of 4-bromo-3-fluorophenylacetonitrile (10.92 mmol, 1.0 eq.), dissolved in 5 ml of dry THF, and 1.49 g of ethylene sulfate (12.0 mmol, 1.1 eq.), dissolved in 5 ml of dry THF, were added in the reactor. The mixture was kept under stirring at T=−20° C. for 4 h and then heated to 20° C. The reaction was quenched by adding $NH_4Cl$ (saturated solution) and extracted with toluene. The organic layer was concentrated to dryness at reduced pressure to yield 3.01 g of crude product (assay=69.4%; molar yield=79.7%).

EXAMPLE 3

Preparation of ethyl 3-fluoro-4-bromo-phenylacetate from 3-fluoro-4-bromo-phenylacetonitrile 2.5 g. of 3-fluoro-4-bromo-phenylacetonitrile substrate, 4.7 g. of ethyl alcohol and 4.7 g. of sulfuric acid were loaded in an reactor at room temperature. The mixture was heated to 100° C. and stirred for 5 hours. When the conversion was completed, the mixture was cooled to room temperature, water and ethyl acetate were added and the aqueous phase was re-extracted with fresh ethyl acetate. The organic phase washed with a sodium bicarbonate/water solution, then with water until pH=7. The organic phase was concentrated to obtain a residue of 2.6 g. of product.

EXAMPLE 4

Cyclopropanation of ethyl 4-bromo-3-fluorophenylacetate (II) with ethylene sulfate (III) to give the ethyl ester of 4-bromo-3-fluorophenyl-cyclopropane carboxylic acid (I)

6.6 ml of lithium diisopropylamide (2M in THF/heptane/ethylbenzene, 13.2 mmol, 2.2 eq.) were loaded into a 50 ml dried reactor at T=−20° C. under nitrogen. 1.71 g of 3-fluoro-4-bromophenylacetate (6.0 mmol, 1.0 eq.), dissolved in 8 ml of dry THF, and 0.82 g of ethylene sulfate (6.6 mmol, 1.1 eq.), dissolved in 8 ml of dry THF, were added dropwise in 10 minutes. The mixture was kept under stirring at T=−20° C. for 3 h then heated to 20° C. and maintained under reflux for 5 h. The mixture was cooled to room temperature. The reaction was quenched by adding $NH_4Cl$ (saturated solution) and extracted with toluene. The organic layer was concentrated to dryness at reduced pressure to yield 1.15 g of crude product (purity=72.4%).

EXAMPLE 5

Cyclopropanation of 4-bromophenylacetonitrile with ethylene carbonate (III) to give 4-bromophenyl-cyclopropane nitrile (I)

40.43 g of ethylene carbonate (459.1 mmol, 30.0 eq.) were loaded at room temperature in a 100 ml reactor. The internal temperature of the reactor was brought to 50° C. After all the solid was melted, 0.153 g of PEG-200 (0.765 mmol, 0.05 eq.) and 3.0 g of 4-bromophenylacetonitrile (15.3 mmol, 1.0 eq.) were charged in the reactor. 5.32 g of potassium tert-butoxide (47.43 mmol, 3.1 eq.) were added portion-wise under stirring to the resulting clear colorless solution. Then, the mixture was heated to 130° C. and kept under stirring for 4 hours. The mixture was cooled to 50° C. and then toluene and deionised water were added. The mixture was kept under stirring for 15 minutes, then stirring was stopped. The aqueous layer was discharged and the organic phase was washed three times with deionised water. The organic layer was concentrated to dryness at reduced pressure to yield 4.31 g of crude product (molar yield=84.0%).

EXAMPLE 6

Cyclopropanation of Different Compounds of Formula (II) with Ethylene Carbonate (III)

Ethylene carbonate (30.0 eq.) was loaded at room temperature in a 100 ml reactor. The internal temperature of the reactor was brought to 50° C. After all the solid was melted, 0.05 eq. of PEG-200 and the compound of Formula (II) (1.0 eq.) (see table 1) were charged in the reactor. 3.1 eq. of potassium tert-butoxide were added portion-wise under stirring to the resulting clear colorless solution. Then, the mixture was heated to 126-135° C. and kept under stirring until complete reaction, for about 4-8 hours. The mixture was cooled to 50° C. and then toluene and deionised water were added. The mixture was kept under stirring for 15 minutes, then the stirring was stopped. The aqueous layer was discharged and the organic phase was washed three times with deionised water. The organic layer was concentrated to dryness at reduced pressure to obtain the end product with a molar yield reported in table 1.

TABLE 1

| X= | Y= | SUBSTRATE (1.0 eq.) | Eq. of ETHYLENE CARBONATE | Eq. of BASE | Eq. of CAT. | REACTION TEMPERATURE | REACTION TIME | YIELD | PURITY |
|---|---|---|---|---|---|---|---|---|---|
| H | CH$_3$S | 4-Me Phenyl ACN | (30.0 eq.) | t-BuOK (3.1 eq.) | PEG-200 (0.05 eq) | 135° C. | 7 h | 91.4% | 92.2% |
| H | CH$_3$O | 4-MeO Phenyl ACN | (30.0 eq.) | t-BuOK (3.1 eq.) | PEG-200 (0.05 eq) | 130° C. | 5 h | 92.4% | 93.2% |
| H | H | Phenyl ACN | (30.0 eq.) | t-BuOK (3.1 eq.) | PEG-200 (0.05 eq) | 126° C. | 5 h | 89.3% | 98.9% |
| H | CH$_3$S | 4-MeS Phenyl ACN | (30.0 eq.) | t-BuOK (3.1 eq.) | PEG-200 (0.05 eq) | 130° C. | 4 h | 83.2% | 97.8% |
| H | Br | 4-Br Phenyl ACN | (30.0 eq.) | t-BuOK (3.1 eq.) | PEG-200 (0.05 eq) | 130° C. | 4 h | 84.0% | 96.6% |
| F | Br | 3-F,4-Br Phenyl ACN | (30.0 eq.) | t-BuOK (3.1 eq.) | PEG-200 (0.05 eq) | 130° C. | 8 h | 83.1% | 84.4% |

The invention claimed is:

1. A process for the preparation of a compound of formula (I):

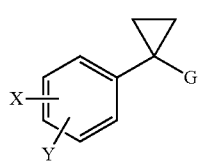

wherein G is —CN or —COOR in which R is a C$_1$-C$_4$ straight or branched alkyl, X and Y are independently selected from the group consisting of hydrogen, fluorine, chlorine, bromine, iodine, R$_1$O— and R$_1$S— wherein R$_1$ is C$_1$-C$_4$ straight or branched alkyl chain; said process comprising the step of reacting a compound of formula (II):

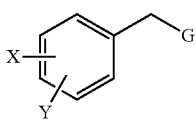

wherein G, X and Y are as defined above with a compound of formula (III):

wherein Z is CO or SO$_2$ in the presence of a base, with the proviso that:
i) when Z is CO the reaction is carried out at a temperature ranging from 120° C. to 180° C. and the molar ratio between the compound of formula (II) and the compound of formula (III) is from 1:10 to 1:30;
ii) when Z is SO$_2$, then G is —COOR$_2$;
to obtain a compound of formula (I) wherein the reaction is carried out in the presence of a compound able to complex alkaline metal cations selected from the group consisting of polyethylene glycols (PEG), phosphonium salts and crown ethers.

2. The process according to claim 1 wherein X is linked to the position 4 and Y to the position 3 of the phenyl ring.

3. The process according to claim 1 wherein G is —CN or —COOEt.

4. The process according to claim 1 wherein Y is hydrogen or fluorine.

5. The process according to claim 1 wherein X is bromine, CH$_3$O— or CH$_3$S— and Y is hydrogen or fluorine.

6. The process according to claim 1 wherein the base is selected from the group consisting of sodium, potassium or lithium tertbutylate, potassium carbonate, sodium hydride, lithium bis(trimethylsilyl)amide (LiHMDS) and Lithium diisopropylamide (LDA).

7. The process according to claim 1 wherein Z is CO.

8. The process according to claim 7 wherein the reaction is carried out at a temperature ranging from 130° C. to 180° C.

9. The process according to claim 7 wherein the molar ratio between the compound of formula (II) and the compound of formula (III) is from 1:20 to 1:30.

10. The process according to claim 1 wherein the compound able to complex alkaline metal cations is selected from the group consisting of PEG-200 and PEG-6000.

11. The process according to claim 1 wherein the compound of formula (II) and the compound able to complex alkaline metal cations are present in a molar ratio ranging from 1:0.02 to 1:2.

12. The process according to claim 1 wherein Z is SO$_2$.

13. The process according to claim 12 wherein the reaction is carried out at a temperature ranging from −20° C. to the reflux temperature.

14. The process according to claim 12 wherein the molar ratio between the compound of formula (II) and the compound of formula (III) is from 1:1 to 1:1.5.

* * * * *